United States Patent
Lee et al.

(10) Patent No.: US 6,921,382 B2
(45) Date of Patent: Jul. 26, 2005

(54) RETRACTING DEVICE FOR A SAFETY SYRINGE

(75) Inventors: Tun-Chi Lee, Hsintien (TW); Ting Shen, Shanghai (CN)

(73) Assignee: Biotop Technology Co., Ltd., Taipei (TW)

( * ) Notice: Subject to any disclaimer, the term of this patent is extended or adjusted under 35 U.S.C. 154(b) by 0 days.

(21) Appl. No.: 10/224,482

(22) Filed: Aug. 21, 2002

(65) Prior Publication Data

US 2004/0039333 A1 Feb. 26, 2004

(51) Int. Cl.[7] .............................. A61M 5/32; A61M 5/50; A61M 5/00; A61M 5/315
(52) U.S. Cl. ........................ 604/110; 604/195; 604/181; 604/225
(58) Field of Search .................................. 604/110, 218, 604/225, 220, 181, 187, 192–198, 128; 128/919; 600/566

(56) References Cited

U.S. PATENT DOCUMENTS

| | | | | | |
|---|---|---|---|---|---|
| 5,575,774 A | * | 11/1996 | Chen | ........................... | 604/110 |
| 5,899,887 A | * | 5/1999 | Liu | ............................. | 604/195 |
| 6,033,385 A | * | 3/2000 | Liu | ............................. | 604/195 |
| 6,117,113 A | * | 9/2000 | Novacek et al. | ............ | 604/195 |
| 6,251,095 B1 | * | 6/2001 | Liu | ............................. | 604/225 |
| 6,461,328 B2 | * | 10/2002 | Wang et al. | ................ | 604/110 |
| 6,488,656 B1 | * | 12/2002 | Wu | ............................. | 604/110 |
| 6,530,903 B2 | * | 3/2003 | Wang et al. | ................ | 604/195 |
| 6,592,555 B1 | * | 7/2003 | Wen-Pi et al. | .............. | 604/181 |

\* cited by examiner

Primary Examiner—Nicholas D. Lucchesi
Assistant Examiner—Roz Maiorino
(74) Attorney, Agent, or Firm—Varndell & Varndell, PLLC

(57) ABSTRACT

A safety syringe has a barrel, a needle hub movably received in the barrel and having a hollow cone with a flange formed on an inner periphery of the hollow cone and a plunger with a hook formed to correspond to the flange of the needle hub such that when the hook engages with the flange of the needle hub, the needle hub is ready to be pulled back into the barrel by a rearward movement of the plunger so that the syringe is ready to be disposed of safely.

3 Claims, 6 Drawing Sheets

RETRACTING DEVICE FOR A SAFETY SYRINGE

BACKGROUND OF THE INVENTION

1. Field of the Invention

The present invention relates to a retracting device for a safety syringe, and more particularly to a retracting device which is able to satisfactorily pull the needle hub back into the barrel so that the syringe is able to be safely disposed.

2. Description of Related Art

A conventional syringe is shown in FIG. 6, and has a barrel (5), a needle hub (6) and a plunger (7).

The barrel (5) has a step (51) formed on an inner face thereof. The needle hub (6) has a flange (61) corresponding to the step (51) and having a diameter slightly larger than a diameter of the step (51). The plunger (7) has a stopper (71) and a hook (72) formed on a distal end of the plunger (7). The needle hub (6) further defines an annular cutout (62) to receive therein an engaging portion (711) of the stopper (71) and a retaining portion (63) formed to maintain the stopper (71) to be in engagement with the needle hub (6). The stopper (71) has an extension (712) extending out of the annular cutout (62) to correspond to the hook (72).

When the needle hub (6) is received in the barrel (5), because the diameter of the flange (61) is larger than the step (51), the diameter of the step (51) is enlarged so that the engagement between the needle hub (6) and the barrel (5) is secured. Then, the engaging portion (711) of the stopper (71) is received in the annular cutout (62) of the needle hub (6).

When the plunger (7) is pushed in the barrel (5) toward the needle hub (6), the hook (72) first passes over the extension (712) of the stopper (71) so as to complete an injection. Thereafter, when the user is pulling the needle hub (6) together with the needle (not shown) back into the barrel (5) in order to safely dispose of the syringe, the hook (72) engages with the extension (712) of the stopper (71) and then the user is able to pull the needle hub (6) together with the stopper (71) inward to the inside of the barrel (5).

However, problems often happen to the users when trying to dispose of the syringe of this type. That is, if the engagement between the flange (61) and the step (51) is too tight, the user will have difficulty pulling the needle hub (6) back into the barrel (5) and if the engagement between the flange (61) and the step (51) is too loose, the needle hub (6) will automatically fall into the barrel (5) when the user is trying to have medicine received inside the syringe. Accordingly, a precise calculation of the dimension of the needle hub (6), the plunger (7) and even the barrel (5) should be taken carefully so that a proper engagement among the needle hub (6), the plunger (7) and the barrel (5) is available.

To overcome the shortcomings, the present invention tends to provide an improved retracting device for a safety syringe to mitigate and obviate the aforementioned problems.

SUMMARY OF THE INVENTION

The primary objective of the present invention is to provide an improved retracting device for a safety syringe so that the user is able to readily pull the needle hub back into the barrel.

In order to accomplish the foregoing objective, the syringe has a barrel, a plunger movably received in the barrel and provided with a hook integrally formed with a stop which is formed on a distal end of the plunger, a needle hub movably received in the barrel and having a flange formed on an inner periphery of the needle hub to correspond to the hook. Engagement between the needle hub and the hook enables the needle together with the needle hub to be readily retracted into the barrel so that accidental damage to the paramedic personnel is prevented.

Other objects, advantages and novel features of the invention will become more apparent from the following detailed description when taken in conjunction with the accompanying drawings.

DETAILED DESCRIPTION OF THE PREFERRED EMBODIMENT

Figure 1:
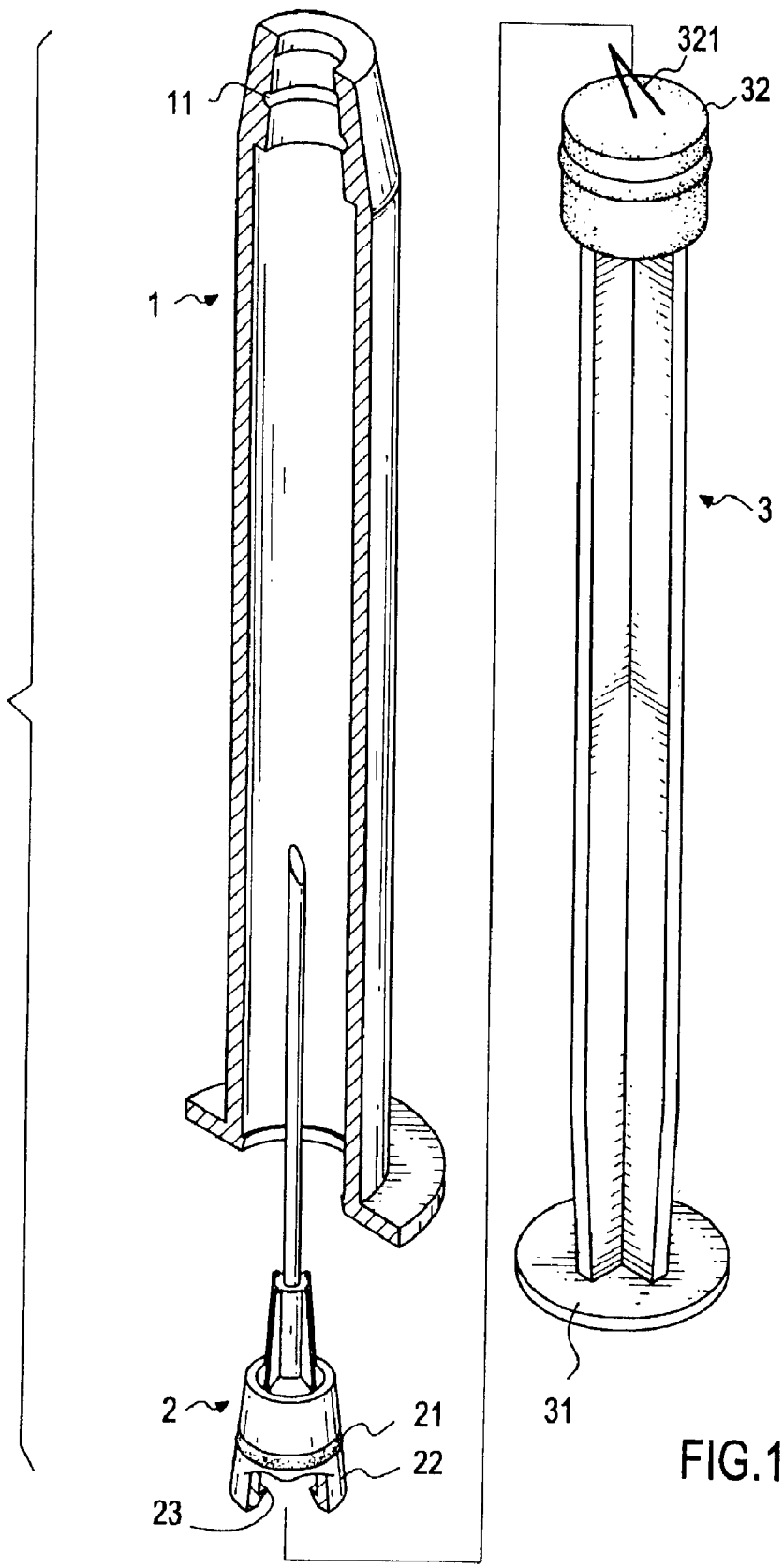
FIG. 1 is an exploded perspective view showing the parts of the syringe of the present invention.

With reference to FIG. 1, the safety syringe in accordance with the present invention has a barrel (1), a needle hub (2) and a plunger (3).

The barrel (1) is hollow inside to receive therein the needle hub (2) and the plunger (3).

Figure 2:
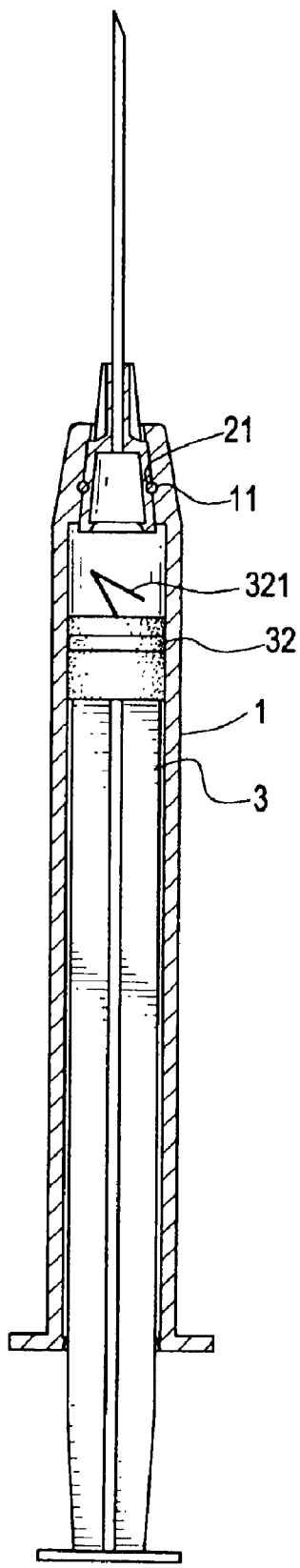
FIG. 2 is a cross sectional view showing an assembly among the barrel, the needle hub and the plunger.

The needle hub (2) has an annular boss (21) formed on an outer periphery of the needle hub (2) and the barrel (1) has an annular recess (11) defined to correspond to the annular boss (21) such that when the needle hub (2) is received in the barrel (1), as shown in FIG. 2, the annular boss (21) is received in the annular recess (11), which allows the needle hub (2) be detachably received in the barrel (1). The needle hub (2) has a hollow cone (22) and a flange (23) formed on an inner periphery of the hollow cone (22) of the needle hub (2).

The plunger (3) has a thumb push (31) formed on a first distal end of the plunger (3) and a stop (32) formed on a second distal end of the plunger (3) and having a hook (321) integrally formed on a front portion of the stop (32) to correspond to the hollow cone (22).

With reference to FIG. 2, when the safety syringe of the present invention is in assembly, the needle hub (2) is first inserted into the barrel (1) to have the annular boss (21) of the needle hub (2) received in the annular recess (11) of the barrel (1) so as to secure a relative position of the needle hub (2) to the barrel (1). Meantime, the plunger (3) is also received in the barrel (1) to be ready to receive medicine in the barrel (1). From FIG. 2 it is noted that before the safety syringe of the present invention is in use, a distance exists between the stop (32) and the hollow cone (22) so that the hook (321) is not in engagement with the flange (23) of the hollow cone (22).

Furthermore, the hook (321) is preferably made of a metal. The hook (321) is bent so that a free end of the hook (321) is resilient relative a distal end securely formed with the stop (32).

Figure 3:
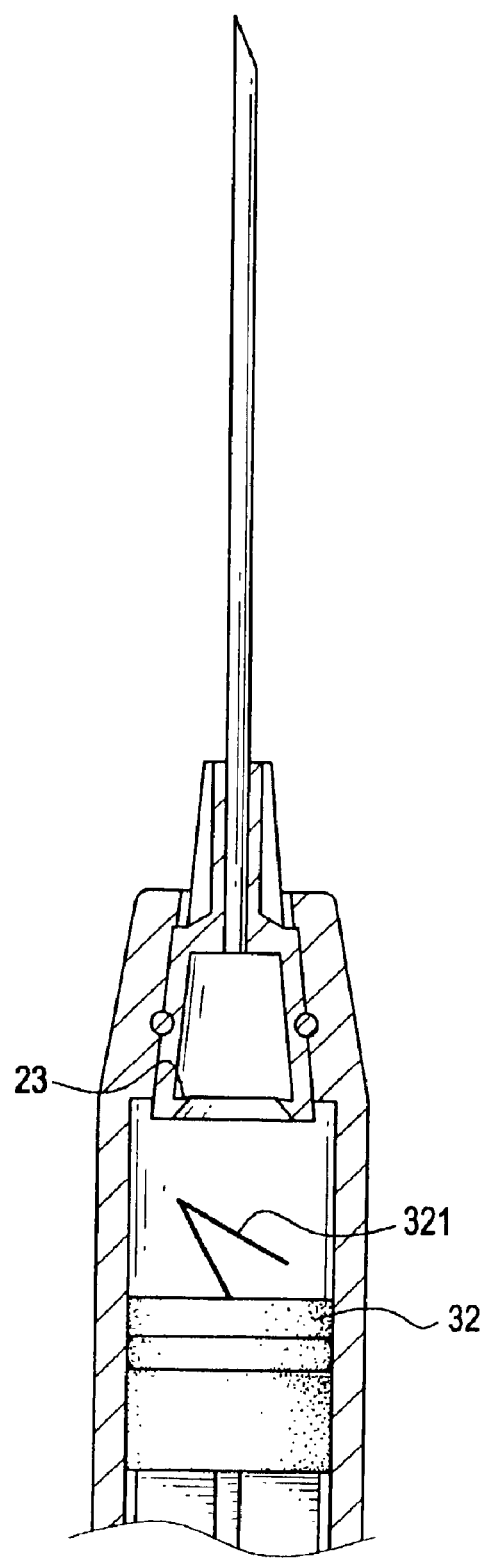
FIG. 3 is a cross sectional view showing the hook engages with the flange of the needle hub.

With reference to FIG. 3, when the medicine inside the barrel (1) is ejected, the user pushes the plunger (3) all the way into the barrel (1) to force the stop (32) to engage with the hollow cone (22). When the stop (32) engages with the hollow cone (22), the hook (321) is received in the hollow cone (22). Because of the resilience of the hook (321), the hook (321) is able to engage with the flange (23) of the hollow cone (22). Thereafter the user is ready to pull the needle hub (2) back into the barrel (1).

Figure 4:
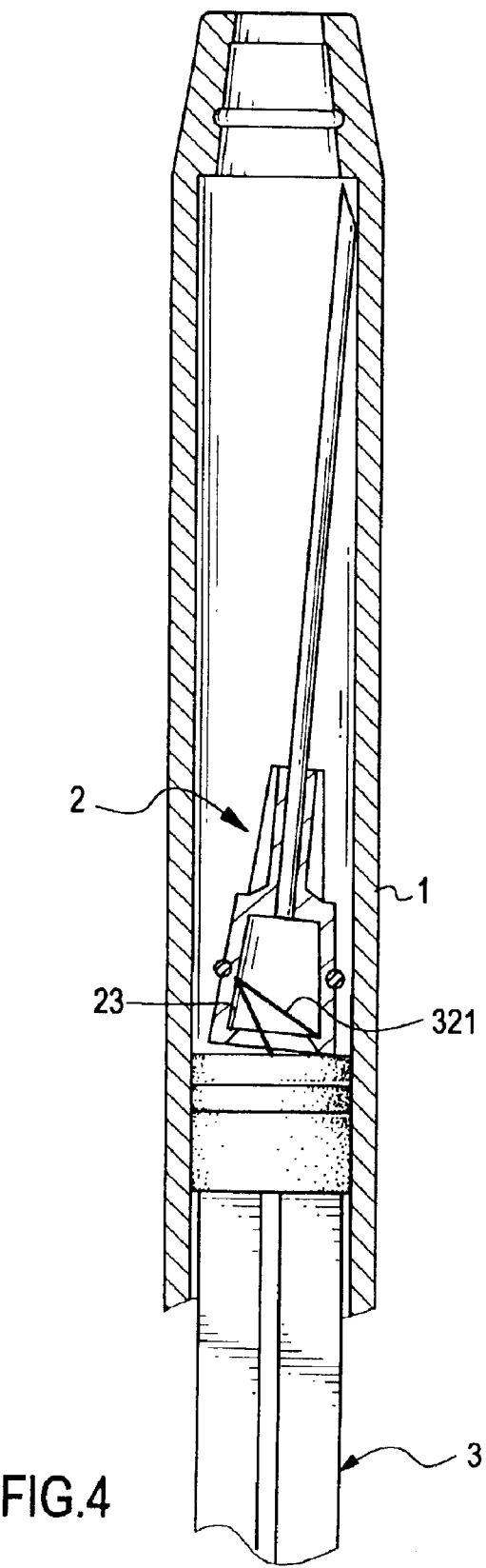
FIG. 4 is a cross sectional view showing that the needle hub is retracted back into the barrel by the reward movement of the plunger.
Figure 5:
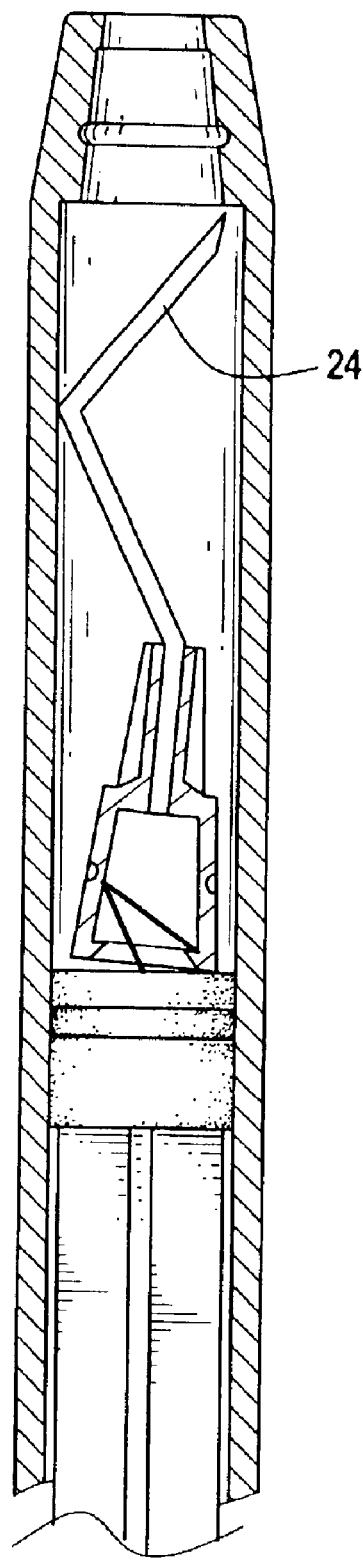
FIG. 5 is a schematic view showing that the needle of the needle hub is broken by the forward movement of the plunger.
Figure 6:
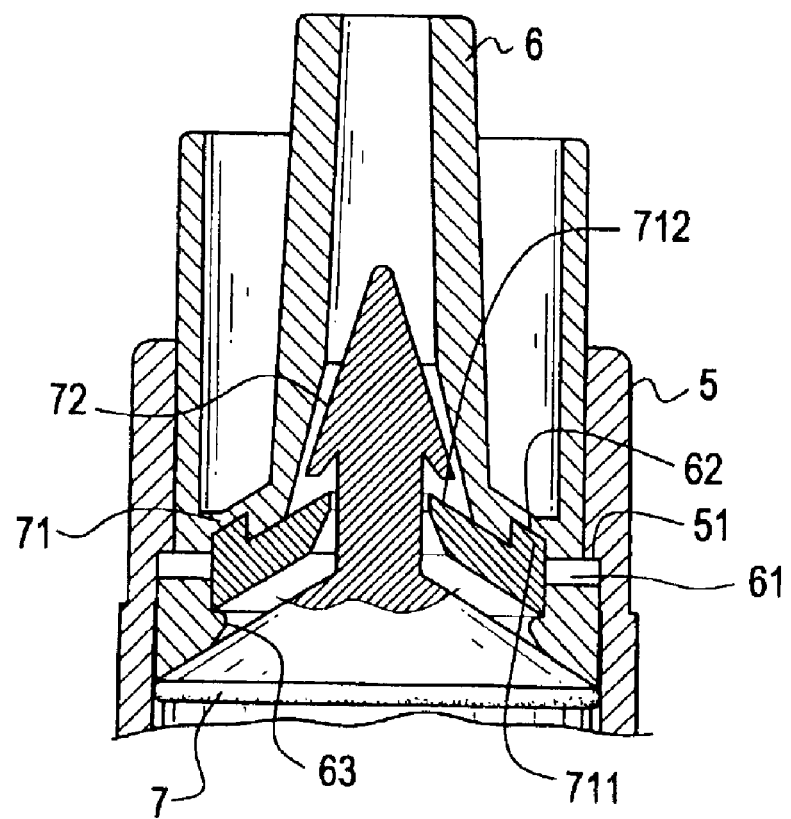
FIG. 6 is a cross sectional view showing the assembly of the barrel, the needle hub, the stopper and the plunger of a conventional safety syringe.

With reference to FIG. 4, after the needle hub (2) is retracted in the barrel (1), because the free end of the hook (321) is in engagement with one point of the flange (23), the needle hub (2) is inclined relative to the barrel (1). When the needle hub (2) is inclined to and fully received in the barrel (1), a forward movement of the plunger (3) together with the needle hub (2), as shown in FIG. 5, results in the needle (24) being bent inside the barrel (1) such that the safety syringe of the present invention is able to be disposed of safely.

It is thus noted that the retracting device used in the safety syringe of the present invention includes the hook (321) formed with the stop (32) and a flange (23) formed on the inner periphery of the hollow cone (22) of the needle hub (2).

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A safety syringe comprising:

a barrel:

a needle hub movably received in and extending out of the barrel, the needle hub having a needle securely attached to a top of the needle hub, the needle having a before use arrangement and an after use arrangement relative to the barrel; in the before use arrangement the needle extends along a central axis of the barrel and out of the barrel, and in the after use arrangement the needle is trapped within the barrel; the needle hub further having a hollow cone integrally formed with the needle hub, the hollow cone having a flange formed on an inner periphery of the hollow cone; and a plunger slidably received in the barrel, the plunger having a thumb press formed on a first distal end of the plunger, and a stop formed on a second distal end of the plunger;

a hook arranged on a free face of the stop of the second distal end of the plunger, the hook being an elongated elastic member having first and second legs with a bent portion between the first and second legs, the first leg of the hook having a fixed end secured to the free face of the stop of the second distal end of the plunger, the second leg of the hook terminating in a free end, the bent portion of the hook forming an apex for the hook where the fixed and free ends of the hook face each other across an unfilled area, the first and second legs and the apex of the hook being arranged at an incline relative to the central axis of the barrel, and the hook of the plunger and the flange of the needle hub cooperating together for switching the needle between the before use arrangement and the after use arrangement;

wherein:

(1) in the before use arrangement the hook of the stop of the plunger is spaced from the needle hub;

(2) during use of the safety syringe, forward movement of the plunger causes the apex of the hook to enter into the hollow cone of the needle hub so that the free end of the hook catches on the flange of the hollow cone of the needle hub; and so that subsequent backward and movement of the plunger pulls the needle hub backward into the barrel only by the action of the hook acting against the flange, and further backward movement of the plunger places the needle in the after use arrangement; and (3) in the after use arrangement, forward movement of the plunger relative to the barrel damages the needle because the hook forces the needle hub together with needle to deviate from the central axis of the plunger causing the needle hub with the needle to engage an inner periphery of the barrel, thereby damaging the needle in rendering the needle safe and unusable.

2. The safety syringe as claimed in claim 1, wherein the hook is made of metal.

3. The safety syringe as claimed in claim 1, wherein the hook has an inverted V shape.

* * * * *